US005957934A

United States Patent [19]
Rapoport

[11] Patent Number: 5,957,934
[45] Date of Patent: Sep. 28, 1999

[54] METHOD AND APPARATUS FOR GUIDING A PENETRATING TOOL INTO A THREE-DIMENSIONAL OBJECT

[75] Inventor: Uri Rapoport, Moshav, Ben-Shemen 17, Israel, 73115

[73] Assignee: Uri Rapoport, Moshav Ben-Shemen, Israel

[21] Appl. No.: 08/996,451

[22] Filed: Dec. 22, 1997

[51] Int. Cl.⁶ .................................................. A61B 19/00
[52] U.S. Cl. .......................... 606/130; 600/417; 600/429
[58] Field of Search ............................ 606/130; 600/424, 600/417, 414, 426, 429, 550

[56] References Cited

U.S. PATENT DOCUMENTS

| | | |
|---|---|---|
| 4,307,944 | 12/1981 | Schirmer . |
| 4,871,966 | 10/1989 | Smith et al. . |
| 5,018,530 | 5/1991 | Rank et al. . |
| 5,078,140 | 1/1992 | Kwoh . |
| 5,142,930 | 9/1992 | Allen et al. . |
| 5,221,283 | 6/1993 | Chang . |
| 5,230,338 | 7/1993 | Allen et al. . |
| 5,246,448 | 9/1993 | Chang . |
| 5,257,998 | 11/1993 | Ota et al. . |
| 5,383,454 | 1/1995 | Bucholz . |
| 5,398,684 | 3/1995 | Hardy . |
| 5,437,280 | 8/1995 | Hussman . |
| 5,483,961 | 1/1996 | Kelly et al. . |
| 5,598,269 | 1/1997 | Kitaevich et al. . |
| 5,628,327 | 5/1997 | Unger et al. . |

OTHER PUBLICATIONS

Article from *The New York Times*, dated Jan. 12, 1999 at p. D7, entitled "Sinus Surgery at Edge of the Brain Gets Safer".
"Mini–transmitters Bug Bugs", *National Geographic*, Jan., 1997.

"Medical Technology Magnet on the Brain", *Scientific American*, Philip Yam, Aug. 1996.

"Stereotactic Radiosurgery & Radiotherapy", *Radiation Oncology*, The Cleveland Clinic Foundation.

"Surgical Procedures for Brain Tumors", Kelly, Patrick J., M.D., FACDS, 1994.

"Array Signal Processing Concepts and Techniques", Johnson et al., Prentice Hall, Inc., 1993, pp. 266–318.

"Radar Handbook", Skolnick, Merrill I., Sec.Ed., MaGraw–Hill Publishing Company, 1990, pp. 3.1–3.39; 349–403.

"Electronics Engineers' Handbook", Christiansen, Donald, 4th Ed., McGraw–Hill, pp. 29–58–29–86.

*Primary Examiner*—Glenn K. Dawson
*Attorney, Agent, or Firm*—Jones, Day, Reavis & Pogue

[57] ABSTRACT

A method and apparatus are described for guiding a penetrating tool to a predetermined point of interest within a three-dimensional object, such as a brain tumor within a human skull. A plurality of signal-transmitting markers disposed about the periphery of the object are used to determine the precise point of entry and slope of entry. A light ray is directed along the slope of entry to the point of entry, and a penetrating tool is directed along the path defined by the light ray. In a preferred embodiment, in which the point of interest is within the brain, additional signal-transmitting markers are placed through a very small skull opening directly at the point of interest and optionally about its periphery. When the skull is opened for surgery and the position of the point of interest in the brain shifts due to loss of pressure, the additional markers nevertheless will indicate the exact location of the point of interest.

19 Claims, 5 Drawing Sheets

METHOD AND APPARATUS FOR GUIDING A PENETRATING TOOL INTO A THREE-DIMENSIONAL OBJECT

FIELD OF THE INVENTION

This invention relates to a method and apparatus for guiding a penetrating tool into a three-dimensional object to reach a point of interest therein. In particular, this invention relates to a method and apparatus for assisting a brain surgeon in guiding a penetrating tool into a brain during surgery to accurately reach a point of interest therein, such as a tumor, and for monitoring the position of the tumor during surgery.

BACKGROUND OF THE INVENTION

One of the most delicate of all surgeries is that in which the skull is opened and the brain is penetrated to reach a point of interest, such as an embedded brain tumor which the surgeon must remove. The surgeon first must determine the location of the tumor, and then determine the optimum point of entry through the skull and into the brain to reach the tumor, taking into consideration the anatomy and physiology of the portions of the brain that will be penetrated, and possible movement of the brain and tumor within the skull resulting from loss of fluid and pressure when the skull is opened. Having selected the point of entry, the surgeon then must select and maintain the proper angle of penetration so that the surgical tools will reach the tumor and be able to remove it.

Recent advances in imaging technologies including magnetic resonance imaging (MRI), computer tomography (CT), and positron emission tomography (PET) have greatly improved the ability to determine non-invasively the structure within almost any portion of the human body. This ability is especially valuable in diagnostics. Such imaging technologies permit the determination of the exact location of a point of interest such as a tumor within a region of the anatomy such as the brain without any preliminary exploratory surgery. Scans of the brain are taken along a series of planes, the data is digitized, and the digitized data can be converted by computer into three-dimensional images showing the size and location of the tumor within the brain. The surgeon then uses this computerized information with other medical knowledge to determine the optimum point of entry into the brain. The computerized information is available to the surgeon during surgery to help the surgeon determine the depth of penetration required to reach the tumor and to estimate the amount of material that must be removed. This diagnostic data cannot, however, monitor changes in position of the brain and tumor within the skull during surgery resulting from loss of fluid and pressure when the skull is opened.

One of the most difficult aspects of brain surgery is estimating and maintaining the slope of entry along which the surgeon should guide the tools through the pre-determined point of entry to the point of interest within the brain. Even when the surgeon has computerized scans showing three dimensional images of the exact pre-surgery location of the point to be reached, determining and maintaining the slope of entry necessary to reach that point inside the brain from the predetermined point of entry is, at best, sophisticated guesswork. Simple geometry dictates that, even when the exact point of entry into the skull is preselected, there are an infinite number of slopes of entry through that point into the brain. The surgeon can only estimate the correct slope of entry and depth of penetration, based on knowledge and years of experience. FIG. 1 illustrates what can happen when a surgeon errs even slightly in estimating or maintaining the slope of entry. As may be seen, the surgeon, even though starting precisely at the preselected point of entry "P" and directing the surgical tools as best as can be determined in the direction of the tumor "T", nevertheless has missed a substantial portion of the tumor to be removed. The surgeon must reposition the penetrating tools through the brain in order to remove the remaining part of the tumor. In addition, except by comparing the amount of material removed with the mass of material apparent from the computerized image, the surgeon cannot determine if all the tumor has been removed.

Accordingly, there is a need for a method and apparatus that will assist in the guidance of a penetrating tool into a solid three-dimensional object to reach a point of interest therein. In particular, there is a need for a method and apparatus that will assist a brain surgeon in guiding a penetrating tool into a patient's brain to reach a point of interest, such as a brain tumor that has previously been identified and located by MRI or other diagnostic techniques.

The following description of the invention throughout this patent specification will be given in terms of a method and apparatus for assisting a surgeon in guiding a penetrating tool to a brain tumor, the location of which has been previously determined by MRI diagnostic techniques, and for monitoring movement of the tumor during the procedure. It will be recognized, however, that the basic principles of the invention are not so limited, and can be applied to any problem dealing with determining and maintaining the slope of entry into a solid three-dimensional object to reach a pre-determined point of interest therein.

SUMMARY OF THE INVENTION

In accordance with the invention, the apparatus for assisting in guiding a penetrating tool into a brain at a particular slope of entry during surgery comprises a plurality of markers capable of being fixedly positioned in a non-coplanar configuration about the periphery of the skull, each of said markers capable of propagating a distinct signal; a receiver capable of receiving and distinguishing the respective signals from the markers; a movable light source capable of emitting a precisely directed ray of light; and a computer for determining whether the slope of the light ray emanating from the source coincides with the desired slope of entry. In accordance with the inventive method, an MRI scan is taken with the markers fixed in position about the skull, the scan including the point of interest within the brain and all the markers, and the data is digitized. From these digitized images, the co-ordinates of the markers relative to the point of interest in three dimensions is measured, and the data is stored in the computer. The patient is brought into surgery, and the light source is placed in the vicinity of the pre-selected desired point of entry, generally along an imaginary line passing through the point of interest within the brain and the point of entry on the skull. The coordinates of the light source are inputted in the computer. The receiver then receives the distinct signals from each of the markers and transmits this information to the computer. Based on this information, the computer calculates the position of the light source relative to each of the markers. Since the position of each of the markers relative to the point of interest in the brain is known and stored in the computer memory, the computer can also calculate the exact position of the light source relative to the point of interest. The position of the light source can be adjusted, and its precise location relative to the markers and thus to the point of interest can be recalculated, until the light source is exactly in line with the point of interest within the brain and the predetermined point of entry on the skull. The light ray emanating from the light source then can be directed to the point of entry along the exact slope of entry which will cause the penetrating tool to reach the point of interest. In one embodiment, the receiver is movable and the light source is mounted directly on the receiver, the receiver is moved in response to instructions received from the computer until the light ray emanating from the light source on the receiver exactly coincides with the desired slope of entry.

The surgeon can then direct the penetrating tools along the exact slope of entry indicated by the ray of light. Preferably, this procedure can be facilitated by the use of a new and inventive apparatus that will be referred to herein as an angular guide means. In one embodiment, the angular guide means comprises a support frame which supports a lockable swivel joint. A hollow guide tube extends through the swivel joint, the guide tube having an inner diameter large enough to accommodate the surgeon's penetration tools yet small enough to provide accurate guidance thereof. The angular guide means is secured in place adjacent the predetermined point of entry. The slope of the hollow guide tube is adjusted by means of the swivel joint until the light ray from the receiver passes exactly through the guide tube, i.e., until the guide tube is directed along the exact slope of entry toward the point of interest, and the swivel joint is locked. The surgeon can then direct the surgical instruments through the fixed guide tube, and know with certainty that the instruments will reach the precise point of interest within the brain.

DESCRIPTION OF THE FIGURES

The invention may be better understood by reference to the following drawings, which are for purposes of illustration only and are not necessarily to scale.

DETAILED DESCRIPTION OF THE INVENTION

Figure 2:
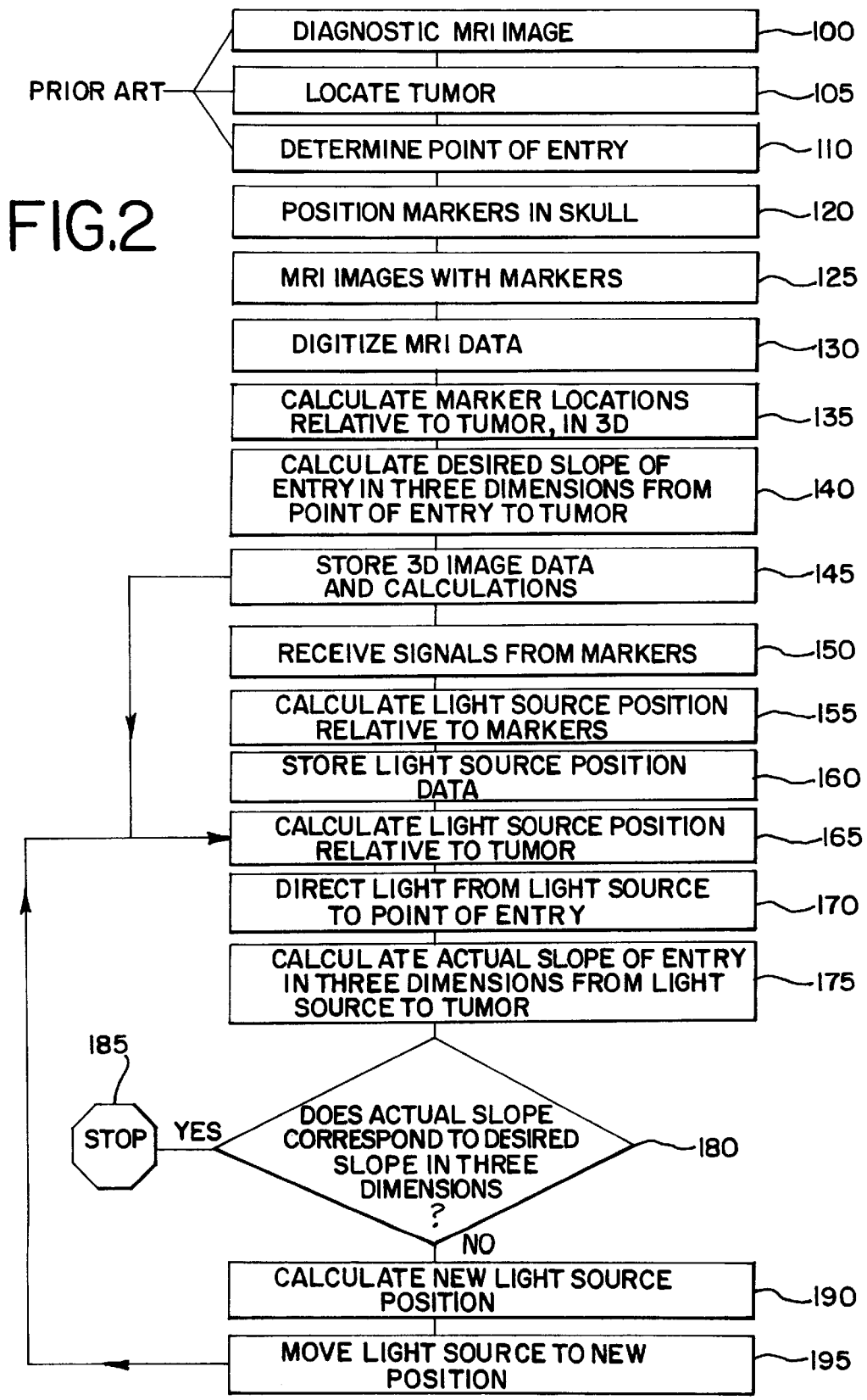
FIG. 2 is a flow chart showing the sequence of steps of the method of the instant invention.

The following description of the method of the instant invention is illustrated schematically in the flow chart of FIG. 2.

The instant invention is to be used for the benefit of any patient who has been diagnosed as having a tumor, aneurysm, or other disorder of the brain which requires surgery directed to a precisely defined spot within the brain. For purposes of illustration only, the disorder requiring surgery will be described as a tumor, although it will be understood that surgery for other disorders of the brain will be greatly aided by the inventive apparatus and method as described herein. According to known techniques, generally indicated as the first three process steps 100, 105, 110 at the beginning of the flow chart of FIG. 2, such a diagnosis will have been confirmed by MRI (or CT or PET) imaging in step 100; further, the MRI (or CT or PET) image will be used in step 105 to exactly pinpoint the location of the disorder within the brain. Based on the size and location of the tumor and other medical, anatomical and physiological considerations, in step 110 the surgeon will determine the desired point of entry through the skull to reach the tumor.

Figure 1:
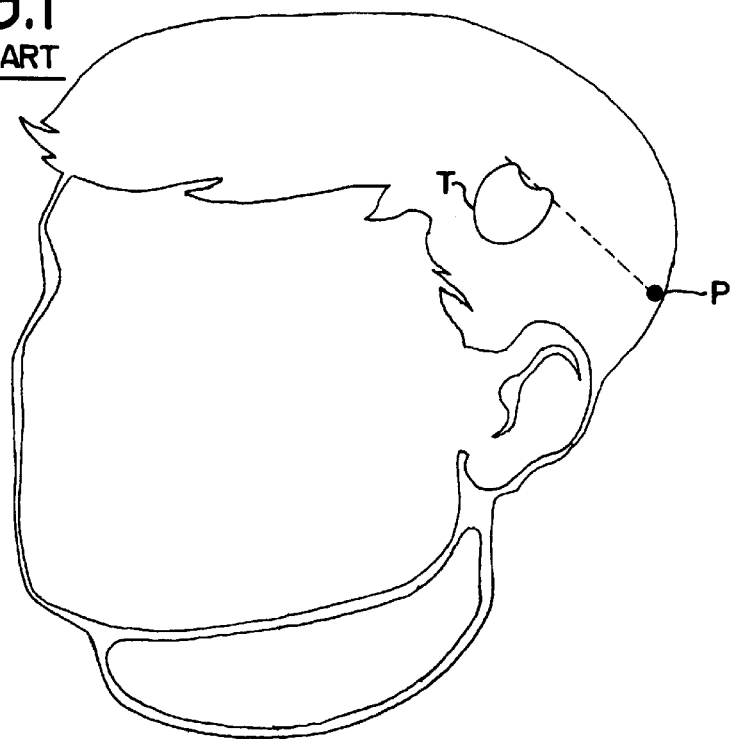
FIG. 1 is an illustration of the problem of the prior art which is addressed by the instant invention, in which the surgeon has inaccurately estimated the slope of entry into the brain, and therefore has missed a substantial portion of the tumor to be excised.
Figure 3:
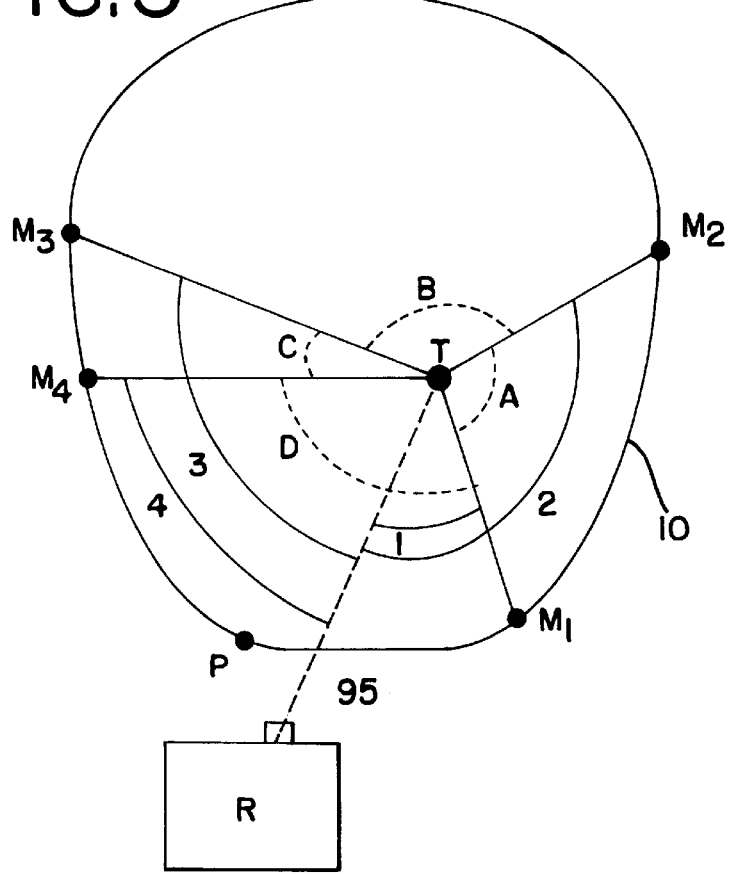
FIG. 3 is a plan diagrammatic view of a patient having a brain tumor to be excised, and showing the positions of the markers and the initial position of the light source.

FIG. 3 is a top plan diagrammatic view showing a patient's head 10 having a brain tumor T which must be surgically excised. Prior to surgery, and now proceeding in accordance with the invention (FIG. 2, step 120) the surgeon has fixedly embedded within the patient's skull in a non-coplanar configuration a plurality of markers, illustrated in FIG. 3 as $M_1$, $M_2$, $M_3$, and $M_4$. It will be recognized, in accordance with the most fundamental principles of geometry, that any three markers will necessarily lie in a plane. The fourth marker, which is not in the same plane as the other three, permits calculations to be made in three dimensions. Additional markers may be used as desired.

A series of MRI images is taken (step 125) with the markers in position. The MRI data is digitized (step 130) and stored in computer 90 (not shown). From the digitized data the computer can calculate the co-ordinates of each marker relative to the center point of tumor T (FIG. 2, step 135). Specifically, the center of the tumor T and each of the markers define a plurality of non-coplanar line segments $M_1T$, $M_2T$, $M_3T$, and $M_4T$ illustrated in FIG. 3; further, the markers define a plurality of non-coplanar line segments $M_1M_2$, $M_1M_3$, $M_1M_4$, $M_2M_3$, $M_2M_4$, and $M_3M_4$, omitted from FIG. 3 for the sake of clarity. From the digitized MRI data, the computer 90 will be able to calculate the exact length of each line segment; then, based on the length of each line segment, the computer will be able to calculate the angles between the line segments defined by the tumor T and the markers. For example, the angles A, B, C, and D indicated by the dotted curves in FIG. 3 are defined by the point sets $M_1$-T-$M_2$, $M_2$-T-$M_3$, $M_3$-T-$M_4$, and $M_4$-T-$M_1$ respectively. The computer will also calculate the angles defined by the point sets $M_1$-T-$M_3$, $M_1$-T-$M_4$, $M_2$-T-$M_3$, $M_2$-T-$M_4$, and $M_3$-T-$M_4$, although curves indicating these angles have been omitted from FIG. 3 for the sake of clarity. It will be appreciated that while FIG. 3 is necessarily a two-dimensional projection of the marker and tumor positions, segments, and angles so described, computer 90 will in fact calculate the segments and angles in three dimensions based on the digitized data from the series of scans and using known principles of solid geometry.

After the MRI scan has been taken with the markers in place, and the various distances and angles described above have been determined and stored in computer 90, the patient is brought into surgery. At this time, based on the previously available MRI data, and further considering anatomical and physiological limitations, the surgeon will already have determined (FIG. 2, step 110) the optimum point of entry, indicated in FIG. 3 as point P, where the skull should be opened and the brain penetrated. Using known methods and a surgical securing frame generally indicated at 22 in FIG. 5, the patient's head is secured in a desired fixed position for the duration of the surgical procedure to allow the surgeon the best possible access to the preselected point of entry P. The exact co-ordinates of point of entry P are entered into computer 90. Referring to FIG. 3, the slope in three dimensions of the line segment PT is the desired slope of entry from the point of entry P to the tumor T. Computer 90 calculates both the length of the line segment PT and its slope, relative to the configuration of fixed markers, FIG. 2, step 140. These values, along with the locations of the markers relative to the tumor T, are stored in computer 90 (FIG. 2, step 145).

Each marker is capable of propagating a distinct signal which can be detected by receiver R, indicated schematically in FIG. 3. Each marker's signal has a unique identifying characteristic, such as phase or frequency, by which the receiver R can distinguish each marker's signal from the others. The receiver-marker system can be either a passive localization system, in which case each marker can be a transmitter which generates a distinct electromagnetic signal which is received by receiver R, or the receiver-marker system can be an active localization system, in which case the receiver actively transmits a radar signal or an array of radar signals toward the markers, and each marker reflects a distinct soundwave signal back to the receiver R. The received signals are then inputted to computer 90, which uses this information to calculate the distance between the receiver R and each marker. The system of receivers and markers can be operated in a manner analogous to the Global Positioning System (GPS), in that the markers around the skull serve the same function as the satellites around the earth. The mathematical and physical principles and techniques useful in passive localization systems are described in D. H. Johnson and D. E. Dudgeon, *Array Signal Processing Concepts and Techniques*, PTR Prentice Hall, 1993, at pages 349–402; *Radar Handbook,* 2nd edition, edited by M. Skolnik, McGraw-Hill Publishing Company, 1990, at pages 3.32–3.38; and *Electronics Engineering Handbook*, by D. Christiansen, 4th edition, McGraw-Hill Publishing Company, 1996, pp. 29.83–29.86. The mathematical and physical principles and techniques useful in active localization systems are described in these same standard reference works, in Johnson et. al. at pp. 266–318; Skolnik at pp. 3.1–3.25 and 5.4–5.32; and Christiansen at pp. 29.58–29.83. All of the foregoing reference works are incorporated herein by reference in their entirety. Those skilled in the art will be able to apply these standard and well-known localization systems to various applications of the method and apparatus of the instant invention.

The receiver R is in the operating room and is operatively linked to computer 90 so as to provide computer 90 with data from the signals received from the markers. Also in the operating room is a movable light source 95, capable of emitting a specifically directed beam of visible light, such as a laser beam. Preferably, the position of light source 95 and the slope of the light ray emanating from light source 95 are adjustable in response to instructions from computer 90. For example, light source 95 may include a swivel ball mechanism to redirect the slope of the ray as instructed by computer 90. The coordinates of movable light source 95 are known to computer 90. This may be accomplished by using an additional marker at light source 95. Alternatively, light source 95 may be built integrally with receiver R as indicated schematically in FIG. 3, and receiver R can be movable in response to instructions from computer 90. The following description of the invention will be with reference to the embodiment in which the light source 95 is integral with movable receiver R. It will be understood that the description of this embodiment is for illustrative purposes only, and is not intended to limit the scope of the invention described and claimed.

Figure 4:
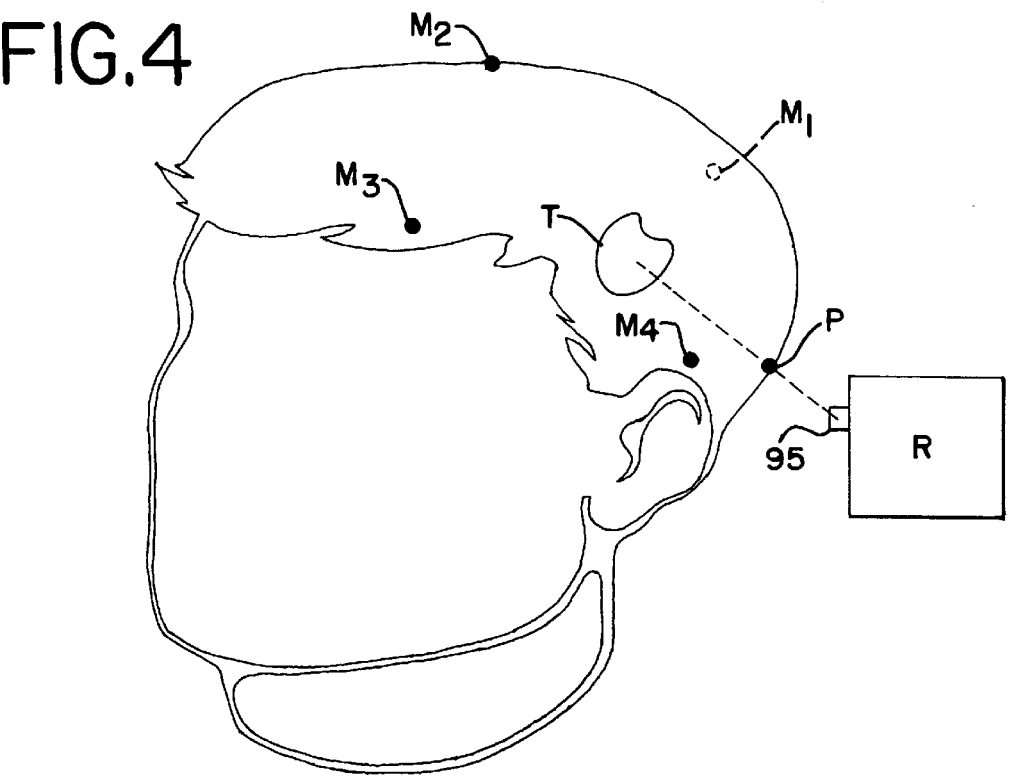
FIG. 4 is an elevation perspective view of the patient having a brain tumor to be excised, showing the marker positions, and showing the light source repositioned to be in line with the tumor and the predetermined point of entry.

In this embodiment, the receiver R with integral light source 95 may be mounted on a robotic arm (not shown), the position of which can also be controlled by computer 90 according to known robotic principles. Initially the receiver R is in an arbitrary position relative to the markers and to the desired point of entry P, as shown generally in FIG. 3. The distinct electromagnetic or sound wave signals are received by receiver R from each of the markers (FIG. 2, step 150) and the values are converted in real time to values corresponding to the distance from a fixed point of origin of light source 95 on receiver R to each of the markers (FIG. 2, step 155), which data is stored in computer 90 (FIG. 2, step 160). These distances correspond to initial line segments $M_1L$, $M_2L$, $M_3L$, and $M_4L$, in three dimensions, which are omitted from FIG. 3 for clarity. (It will be understood in the discussion which follows that "L" refers to the position of the light source, whether or not integral with the receiver, and the distances between L and either the tumor T or markers M are all based on the specific position of light source 95). Based on these distances, and the known position of each of the markers relative to the tumor T, computer 90 then calculates the position of light source 95 relative to the tumor T (FIG. 2, step 165), i.e., it calculates the length and slope of the line segment LT between the light source 95 and tumor T, indicated as a dashed line in FIG. 3. Light source 95 then emits a ray directed generally toward point of entry P (FIG. 2, step 170). Computer 90 then calculates (FIG. 2, step 175) the light ray's actual point of entry and actual slope of entry in three dimensions. The computer then determines (FIG. 2, step 180) if the actual point of entry and actual slope of entry of the light ray correspond to the line defined by the surgeon's preselected point of entry P and desired slope of entry, i.e., computer 90 determines if the line segment LT intersects the point P and has the same slope as the line segment PT. If it does, then the light source 95 is in the correct position, and it is locked in place (FIG. 2, step 185). If the light source is not in the correct position, then computer 90 calculates where the light source 95 should be repositioned (FIG. 2, step 190) so that LT will be closer to the desired point and slope of entry. Light source 95 is then repositioned (FIG. 2, step 195), such as by means of the robotic arm. Once again, based on the signals received by the receiver R from each of the markers $M_1$, $M_2$, $M_3$, and $M_4$, the new position of the light source 95 relative to the tumor can be calculated (i.e., the computer software loops back to step 165 in FIG. 2), and the new actual point and slope of entry can be calculated and compared with the desired point and slope of entry values preselected by the surgeon. As shown by the loop in the flow chart of FIG. 2, this process is repeated as often as necessary until the correct position of the light source 95 is attained, as shown in FIG. 4.

When the light source 95 is in the correct position, a light ray such as a laser is directed from the rotatable light source 95 to the exact point of entry P and along the exact desired slope of entry. The proper orientation of the light source 95 can be directed by computer 90. This light ray guides the surgeon. First, the surgeon must cut away a portion of the skull to allow access to the brain. The surgeon will be able to remove a substantially smaller portion of skull than would have had to have been removed without the use of the instant invention, because the desired point of entry will be known very accurately, and will be indicated clearly by the light ray. Whereas typically 2–3 square inches or more of skull would have had to have been removed, when the apparatus and method of the instant invention are used the area of skull to be removed can be one square inch or even less.

After the skull has been opened, the light ray is then used to guide the surgeon in actual penetration of the brain. Thus, even though any marker that may have been placed on the skull directly at the point of entry P will have been removed, the light ray will still be directed to the point of entry on the soft brain tissue. In one embodiment of the invention, the penetrating tool is simply equipped on one end with an indicating means such as a reflector; as long as the light ray is reflected back to the light source 95, then the surgeon knows that the tool is being held at the correct slope of entry to reach the tumor. If the tool is not held at the correct angle, then light will not be reflected back and an audible alarm can be activated. This will guide the surgeon in reorienting the tools along the desired slope of entry.

Figure 5:
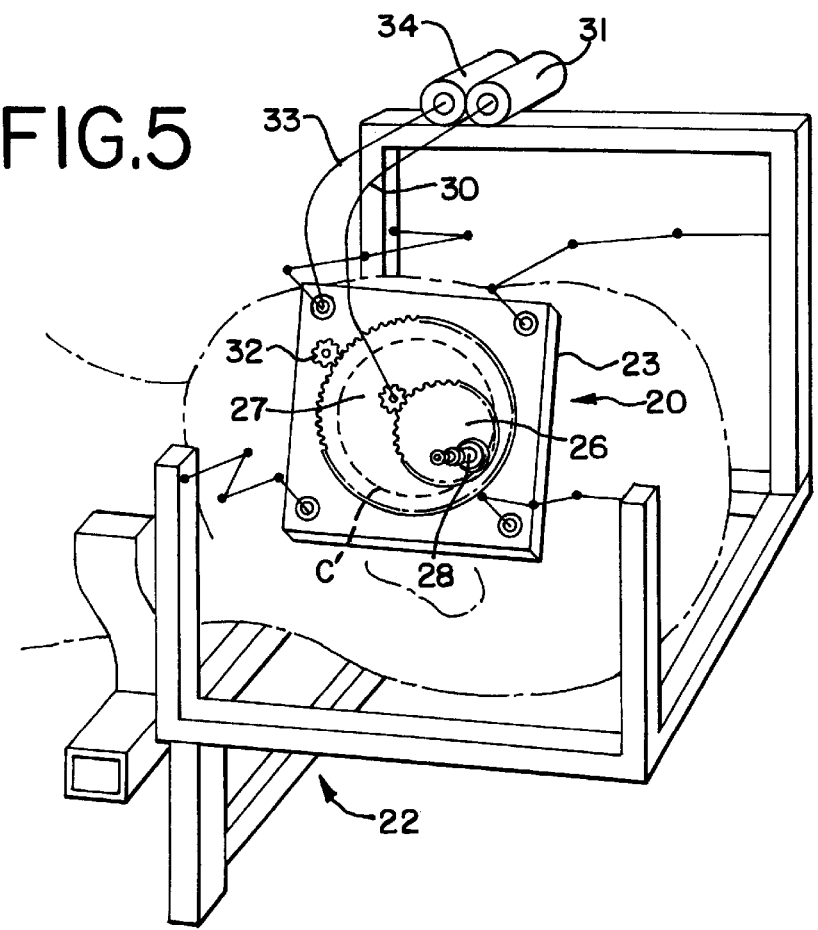
FIG. 5 is a perspective view showing the angular guide means in position to guide the surgeon in introducing the surgical tools into the patient's brain.
Figure 6:
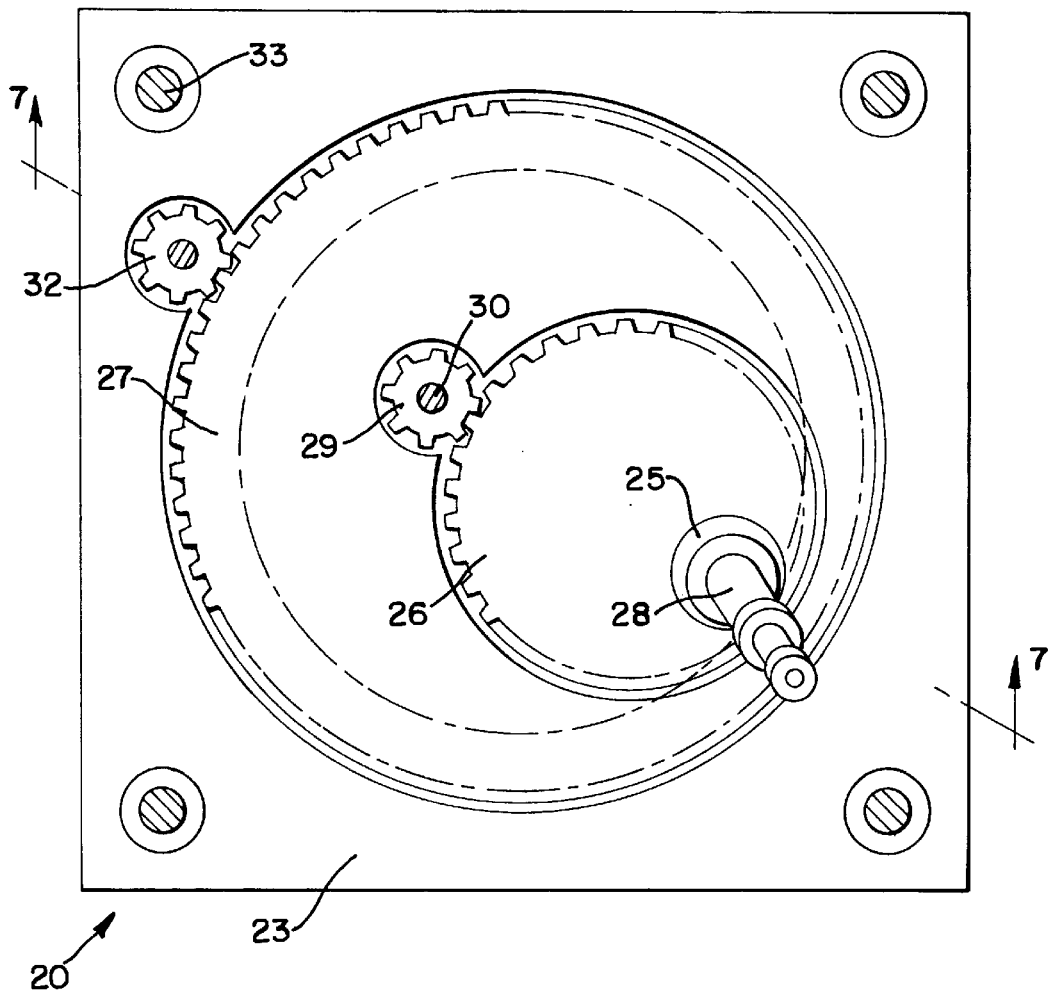
FIG. 6 is a top plan view of the angular guide means.
Figure 7:
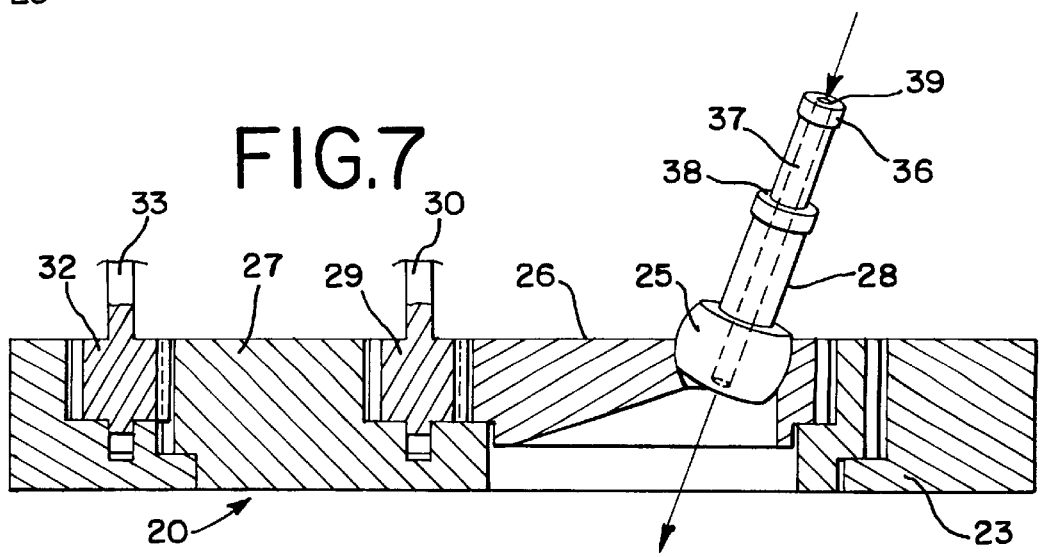
FIG. 7 is a cross-sectional side view of the angular guide means.

In a preferred embodiment of the invention, an apparatus known as an angular guide means is used in conjunction with the light ray to guide the surgeon. As shown in FIGS. 5–7, the angular guide means 20 comprises a support frame 23 which is removably fixed to a portion of the surgical securing frame 22 used to secure the patient in the desired operating position. Support frame 23 supports a lockable swivel joint 25 through which extends a hollow guide tube 28. In one embodiment, swivel joint 25 can be eccentrically mounted in rotatable gear 26, which in turn is eccentrically mounted in rotatable gear 27. Gear 26 is rotated by means of gear 29 which is operated by shaft 30 and powered by motor 31; gear 27 is rotated by means of gear 32 which is operated by shaft 33 and powered by motor 34. By cooperative rotation of gears 26 and 27, swivel joint 25 can be positioned accurately substantially anywhere within the area of gear 27 indicated by dotted circle C.

Support frame 23 is fixed in position such that swivel joint 25 intersects the light ray from source 95. If the coordinates of a fixed point on angular guide means 20 is known to computer 90, either by inputting or by measuring with a marker, then computer 90 can signal motors 31 and 34 to rotate gears 26 and 27 so as to position swivel joint 25 to exactly intersect line segment RT. Guide tube 28 is rotated through swivel joint 25 until the light ray passes uninterrupted through guide tube 28. The proper orientation of guide tube 28 can be determined visually, by simply observing the light reaching the point of entry P, or proper orientation could be aided by use of an audible alarm such as described above with respect to the use of the surgeon's hand tools. Once the guide tube 28 is in proper position and slope, swivel joint 25 is locked in place. Optionally, the receiver R and/or light source 95 then can be removed to allow the surgeon ease of access to the surgical site.

Figure 8:
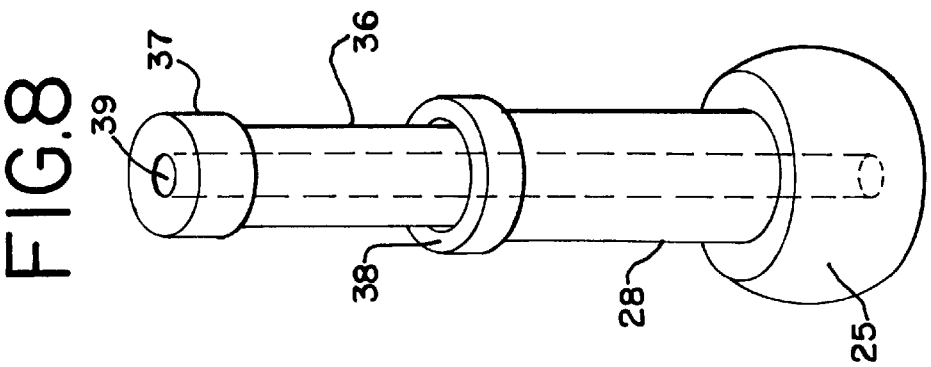
FIG. 8 is a partially exploded detailed view of an embodiment of the hollow guide tube.

The inner diameter of guide tube 28 is narrow enough to allow the light ray to accurately determine the orientation of the guide tube along the desired slope of entry, yet wide enough to accommodate the surgeon's tools and instruments. In the embodiment of the guide tube illustrated in FIG. 8, guide tube 28 is provided with insert 36, such that the outer diameter of insert 36 fits within the inner diameter of guide tube 28, and such that the lip 37 of insert 36 fits on the upper shoulder 38 of guide tube 28. Insert 36 is provided with narrow bore 39; when light from source 95 passes uninterrupted through narrow bore 39, then it is known that guide tube 28 is very accurately positioned along the correct slope of line segment RT. Guide tube 28 is then locked in place, insert 36 is removed, and the surgeon can direct the penetration tools through guide tube 28 and into the brain, exactly toward the tumor. Further, the MRI data will allow precise calculation by computer 90 of the distance between the point of entry P and the tumor T. Therefore the surgeon will know exactly how deeply to penetrate the tools into the brain to reach the tumor T.

The method and apparatus of the instant invention can be enhanced by the use of additional markers. In one embodiment of the invention, a marker can be placed precisely at the desired point of entry P. Such a placement can facilitate the accurate calculation of the slope of entry, and the accurate positioning of the light ray and guide tube.

Figure 9:
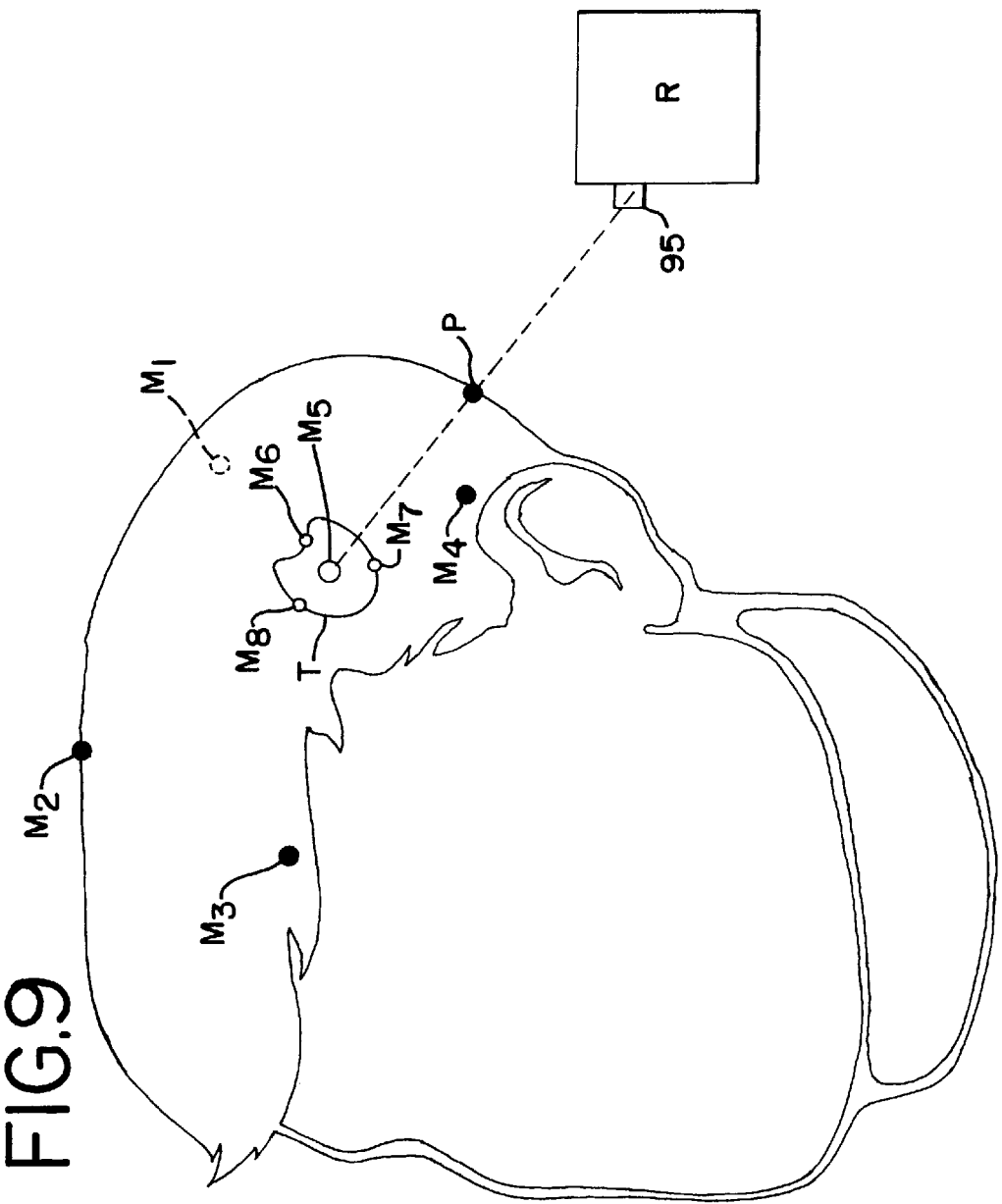
FIG. 9 illustrates an embodiment of the invention wherein additional markers are also positioned within and at the periphery of the tumor to be excised.

In a preferred embodiment of the invention, in addition to the external markers previously described, one or more markers can be positioned internally within the brain during surgery, either at the tumor periphery, or at the tumor center, or both. It is known that when a portion of the skull is removed, fluid is inevitably lost, resulting in a loss of intracranial pressure. This loss of fluid and pressure may cause shifting of the brain within the skull, resulting in a change of location of the tumor, such that at the moment of penetration of the brain the tumor is no longer at the precise position indicated by the pre-surgery MRI image. Furthermore, the surgeon usually will prefer to begin excision from the inside of the tumor at its center, which will cause the tumor to collapse inwardly, so that the surgeon will not have to contact healthy brain cells just beyond the tumor periphery. To address these concerns, prior to opening the skull a slope of entry is determined by the method described above, not only with respect to the center of the tumor, but also with respect to points in the vicinity of the tumor, and preferably on the tumor periphery. Then, prior to removal of a portion of the skull, a thin needle carrying an internal marker is inserted through a small hole in the skull and into the brain, and the marker is implanted exactly at the tumor periphery. The hole in the skull through which the internal marker is inserted is very small, so that there will be substantially no loss of fluid or pressure. These steps can be repeated to place additional markers at other points along the tumor periphery, as desired. An internal marker can also be placed at the center of the tumor. FIG. 9 illustrates the patient having a brain tumor to be removed and having external markers $M_1$, $M_2$, $M_3$, and $M_4$ embedded in the skull, marker $M_5$ at the center of the tumor T, and markers $M_6$, $M_7$ and $M_8$ at points along the periphery of tumor T. The skull is then opened, and even if the position of the tumor has shifted due to loss of fluid and pressure, it will be possible to determine the tumor's precise shift in location because of the internal markers' distinct signals which will be recognized by the receiver R and converted in real time into three-dimensional positional data by computer 90. The light source 95 can then be repositioned in accordance with the general method as explained above to establish a corrected slope of entry, and if necessary, a corrected point of entry P to reach the tumor in its new position. Then, as the tumor is extracted from its center, it will collapse inwardly and the additional markers will be extracted with it. Moreover, since the additional markers were positioned at the tumor periphery, the removal of the peripheral internally placed markers will indicate to the surgeon that substantially all of the tumor has been removed.

When the method of the instant invention is practiced with both external and internal markers as described, it is possible to combine phase detection techniques and radar detection techniques, i.e., the external markers can operate by transmitting signals of different phases and the internal markers can operate by radar, or vice versa.

While the invention has been described in terms of a method and apparatus for assisting a surgeon in guiding penetrating tools to a tumor during surgery, using information from MRI scans, it will be appreciated that this description is for purposes of illustration, not limitation. As already mentioned, the light source 95 need not be mounted directly on receiver R; CT or PET images may be used instead of MRI images; and the receiver/marker system may function either actively (radar-based) or passively (based on electromagnetic transmitters). The number, placement, and type of markers can be varied, all within the scope of the instant invention.

The light source 95, whether or not on receiver R, may be moved either by a robotic arm, or by other known means such as a cross-bar system such as are used in X-Y plotters. Such a cross-bar system may also be used instead of the rotating gear system to position the guide tube of the angular guide means.

The instant invention also has utility in applications beyond the field of medicine. For example, the principles of the invention can be applied to geological projects or other projects involving drilling toward a pre-determined location within the earth. Industrial applications for situations requiring precise penetration of a three-dimensional object will also be apparent.

What is claimed is:

1. A system for directing a penetrating tool through a three-dimensional object from a known point of entry and along a desired slope of entry to a known point of interest within the object, the apparatus comprising
   (a) a plurality of peripheral markers suitable for placement about the periphery of the object, each peripheral marker capable of propagating a distinct signal;
   (b) one or more internal markers suitable for placement within the object in the vicinity of the point of interest and in fixed relation thereto, each internal marker capable of propagating a distinct signal;
   (c) a receiver capable of receiving and distinguishing the signals propagated by each of said peripheral and internal markers;
   (d) a movable source of a light ray, the light ray being directable along a slope to intersect the object;
   (e) a computer means adapted to receive information relating to said signals from said receiver and able to calculate and store the location coordinates of each of said peripheral and internal markers with respect to one another, said computer means further adapted to receive the location coordinates of said light source, and to indicate whether the light ray's point of intersection with said object and slope correspond to the known point of entry and desired slope of entry, whereby the light ray can guide a penetrating tool through the known point of entry and along the desired slope of entry to the known point of interest.

2. The system of claim 1 further including a radar transmitter to which one or more of said markers respond in a unique manner so as to propagate distinct soundwave signals.

3. The system of claim 2 wherein said radar transmitter is integral with said receiver.

4. The system of claim 1 wherein one or more of said markers is a transmitter which propagates its own distinct electromagnetic signal.

5. The system of claim 1 wherein said light ray source is movable in response to signals received from said computer.

6. The system of claim 5 wherein said light ray source is integral with said receiver, and said receiver is movable in response to signals received from said computer mean.

7. The system of claim 1 wherein said apparatus is adapted for assisting a surgeon in directing a penetrating tool along the desired slope of entry into a skull to the known point of interest.

8. The system of claim 7 wherein said peripheral markers are adapted to be fixedly positioned in the skull.

9. The system of claim 7 wherein said one or more internal markers are suitable for placement at pre-determined locations within the brain.

10. The system of claim 1 further including an angular guide means, said angular guide means comprising a guide tube lockable in an orientation coincident with the desired slope of entry as indicated by said light ray, whereby tools directed through said guide tube will necessarily be guided along said desired slope of entry.

11. A guide means for guiding a tool along a predetermined slope, said guide means comprising
   a support frame,
   a movable positioning means supported by said support frame, said movable positioning means comprising a first rotating gear and a second rotating gear of smaller diameter than said first rotating gear and eccentrically mounted within the circumference thereof, and
   a hollow guide tube pivotably mounted eccentrically in said second rotating gear and capable of being maintained fixedly oriented along said predetermined slope, said first and second rotating gears cooperating to position the pivotable mounting of said hollow guide tube at a predetermined point intersecting said predetermined slope, so that a tool positioned within said guide tube will be directed along said predetermined slope.

12. The guide means of claim 11 further including a removable insert coaxial with said hollow guide tube, said insert having an inner bore for precisely orienting said guide tube along said predetermined slope, said insert capable of being removed to allow a tool to be positioned within said guide tube.

13. A method for directing a penetrating tool through a known point of entry and along a desired slope of entry to a known point of interest within a three-dimensional object, comprising
   (a) locating a plurality of peripheral markers about the periphery of the object, each marker capable of propagating a distinct signal,
   (b) providing one or more internal markers within the object in the vicinity of the point of interest and in fixed relation thereto,
   (c) providing a receiver capable of receiving and distinguishing the respective signals propagated by each of said peripheral and internal markers,
   (d) determining the co-ordinates in three dimensions of each of said markers relative to the known point of interest,
   (e) positioning a movable source of a light ray such that said light ray is directed generally toward said point of entry,
   (f) determining the co-ordinates of said light ray source and the orientation of said ray of light relative to the known point of interest,
   (g) determining from said co-ordinates whether said ray of light intersects said known point of entry and along said desired slope of entry,
   (h) repeating steps (e)–(g) until said ray of light does intersect said point of entry along said desired slope of entry, and (i) using said ray of light to guide a penetrating tool along said desired slope of entry at said known point of entry.

14. The method of claim 13 wherein one or more of said markers is a transmitter that propagates a distinct electromagnetic signal.

15. The method of claim 14 further including the step of providing a source of radar waves, one or more of said markers being responsive to said radar waves to propagate a distinct sound wave signal.

16. The method of claim 13 wherein said three-dimensional object is a skull and the method assists a surgeon in guiding a penetrating tool into the brain.

17. The method of claim 16 wherein the coordinates of said peripheral markers relative to the point of interest are determined from imaging scans taken with said markers in fixed positions.

18. The method of claim 17 wherein said imaging scans are selected from the group consisting of magnetic resonance imaging, computer tomography, and positron emission tomography.

19. The method of claim 13 wherein step (i) is accomplished by orienting a hollow guide tube such that said light ray passes therethrough, and directing the penetrating tool through the guide tube.

* * * * *